United States Patent
Heard et al.

(10) Patent No.: US 9,468,493 B2
(45) Date of Patent: Oct. 18, 2016

(54) APPARATUS, SYSTEM, AND METHOD FOR PERFORMING SURFACE TISSUE DESICCATION HAVING AN INTERNAL COOLING SYSTEM

(75) Inventors: David N. Heard, Boulder, CO (US); Joe D. Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 726 days.

(21) Appl. No.: 13/343,158

(22) Filed: Jan. 4, 2012

(65) Prior Publication Data

US 2013/0172876 A1 Jul. 4, 2013

(51) Int. Cl.
 *A61B 18/14* (2006.01)
 *A61B 18/00* (2006.01)

(52) U.S. Cl.
 CPC .... *A61B 18/148* (2013.01); *A61B 2018/00023* (2013.01); *A61B 2018/1407* (2013.01)

(58) Field of Classification Search
 CPC .......... A61B 18/02; A61B 2018/0212; A61B 2018/0262; A61B 18/00; A61B 2018/00011; A61B 2018/00029; A61B 2017/00022; A61B 2018/00863; A61B 18/0218; A61B 2018/00666; A61B 2018/00744; A61B 2018/00005; A61B 2018/0268; A61B 2018/0091; A61B 2018/00916; A61B 2018/00922; A61N 1/08; A61F 7/12; A61F 2007/126; A61F 2007/0054; A61F 7/00; A61M 5/44; A61M 2205/366; A61M 2206/10; A61M 5/00
 USPC ....................... 606/20–23, 25–26, 32, 34, 41
 See application file for complete search history.

(56) References Cited

U.S. PATENT DOCUMENTS

| | | | |
|---|---|---|---|
| 5,647,871 A | 7/1997 | Levine et al. | |
| 5,688,267 A | 11/1997 | Panescu et al. | |
| 5,829,519 A | 11/1998 | Uthe | |
| 5,951,546 A | 9/1999 | Lorentzen | |
| 6,056,745 A | 5/2000 | Panescu et al. | |
| 6,068,629 A | 5/2000 | Haissaguerre et al. | |
| 6,074,389 A | 6/2000 | Levine et al. | |
| 6,206,876 B1 | 3/2001 | Levine et al. | |
| 6,322,584 B2 | 11/2001 | Ingle et al. | |
| 6,416,491 B1 | 7/2002 | Edwards et al. | |
| 6,432,104 B1 | 8/2002 | Durgin et al. | |
| 6,626,832 B1 | 9/2003 | Paltieli et al. | |
| 6,679,882 B1 | 1/2004 | Kornerup | |
| 7,074,219 B2 | 7/2006 | Levine et al. | |
| 7,255,696 B2 | 8/2007 | Goble et al. | |
| 7,303,558 B2 * | 12/2007 | Swanson ........................ | 606/41 |
| 7,322,975 B2 | 1/2008 | Goble et al. | |
| 7,708,735 B2 | 5/2010 | Chapman et al. | |
| 7,879,031 B2 | 2/2011 | Peterson | |
| 2006/0009759 A1 | 1/2006 | Chrisitian et al. | |
| 2007/0083198 A1 | 4/2007 | Ein-Gal | |
| 2009/0248006 A1 | 10/2009 | Paulus et al. | |
| 2009/0306659 A1 | 12/2009 | Buysse | |
| 2010/0114086 A1 | 5/2010 | Deem et al. | |

\* cited by examiner

*Primary Examiner* — Deborah Malamud

(57) ABSTRACT

Three types of internal cooling mechanisms for cooling one or more electrodes of a surface tissue desiccation device are described. Each cooling mechanism is closed-ended thereby preventing the cooling fluid from being dispensed from an electrosurgical handset of the device and onto the surgical site. The cooling fluid re-circulates in a conduit or lumen assembly between a fluid source, such as a fluid reservoir, and the electrode(s) at a distal end of the electrosurgical handset. A method is also provided for performing an electrosurgical procedure using the surface tissue desiccation device. The method includes activating an energy source; causing one or more electrodes to heat tissue; and internally cooling at least a portion of the at least one electrode(s) via an internal cooling mechanism. The internal cooling mechanism keeps the electrode(s) in a cooled state during the electrosurgical procedure, such as surface tissue desiccation.

23 Claims, 5 Drawing Sheets

APPARATUS, SYSTEM, AND METHOD FOR PERFORMING SURFACE TISSUE DESICCATION HAVING AN INTERNAL COOLING SYSTEM

BACKGROUND

1. Technical Field

The present disclosure relates to an apparatus, system and method for performing an electrosurgical procedure. More particularly, the present disclosure relates to an apparatus, system and method for performing surface tissue desiccation which employs an electrosurgical apparatus that includes an internal cooling mechanism for cooling one or more electrodes during operation thereof.

2. Description of Related Art

Electrosurgical apparatuses (e.g., surface tissue desiccation devices) are well known in the medical arts and typically include a handset with an on/off switch, a shaft and at least one electrode operatively coupled to a distal end of the shaft that is configured to perform an electrosurgical procedure, such as surface tissue desiccation. The electrosurgical apparatuses utilize electrical energy to effect hemostasis by heating the tissue and blood vessels to coagulate, cauterize, seal, cut, desiccate and/or fulgurate tissue.

Electrosurgical apparatuses and instruments, such as surface tissue desiccation devices, require a cooling mechanism to keep the one or more electrodes in a cooled state while activating RF power between the electrodes. Typical cooling mechanisms deliver a cooling medium, e.g., a suitable sterile solution such as water, saline and the like, to the electrodes via an open lumen system, as shown by FIG. 1, which enables the coolant to be delivered to the electrodes and dispensed onto the electrodes and the surgical field, and thereby cool the electrodes. Besides, the cooling medium ensuring that the electrodes remain in a cooled state, the cooling medium causes the effective contact impedance between the tissue and the electrodes to remain low, thus reducing sticking and charring while promoting maximum surgical effect in the tissue. Due to the electrodes being heated, the portion of the cooling medium dispensed or discharged onto the electrodes is converted to a gas, such as steam. The gas and the liquid cooling medium which is not converted to steam may impede the surgeon by obscuring the surgical site.

As shown by FIG. 1, the distal end of a known electrosurgical handset 10 for performing an electrosurgical procedure, such as surface tissue desiccation, includes two electrodes 12, 14 which become heated during an electrosurgical operation. A cooling mechanism 13 having a tubing assembly or lumen assembly 16 with two metal conduits 24, 26 defined therein delivers cooling fluid from a cooling fluid reservoir 28 to each respective electrode 12, 14 as shown by arrows A. Each conduit 24, 26 has an exit 18, 20 at a distal end of each electrode 12, 14 for dispensing the cooling fluid onto the electrodes 12, 14 and the surgical site. An insulator tubing assembly 30 insulates a major portion of the metal conduits 24, 26, leaving only the electrodes exposed, at the distal end of the handset 10. An on/off switch 13 controls the operation of the handset 10.

SUMMARY

An aspect of the present disclosure is to provide an electrosurgical apparatus, such as a surface tissue desiccation device, having an internal cooling mechanism for cooling one or more electrodes during an electrosurgical operation, such as surface tissue desiccation. According to the present disclosure, an electrosurgical apparatus is provided having an internal cooling mechanism for delivering a cooling medium via one or more conduits or lumens to at least one electrode at a distal end of an electrosurgical handset. The handset can be of the type used to treat muscle and bone in orthopedic procedures including total joint replacement and spine surgery. An added advantage of the present disclosure, besides improving visibility to the surgical site by not dispensing the cooling medium onto the electrodes, is that the internal cooling mechanism reduces the need for suction of the surgical site.

The present disclosure describes three types of internal cooling mechanisms for an electrosurgical apparatus or device. One of ordinary skill in the art may adapt the teachings of the present disclosure to other types of internal cooling mechanisms. The three types of internal cooling mechanisms described herein in accordance with aspects of the present disclosure include: monopolar loop, bipolar loop, and bipolar isolated cooling mechanisms. The monopolar loop cooling mechanism has cooling fluid flowing internally through a handset via a closed loop lumen configuration provided by a tubing or conduit assembly to the distal end of the handset. A portion of a metallic conduit of the closed loop lumen configuration extends beyond the distal end of the handset. The major portion of the conduit extending beyond the distal end of the handset is uninsulated and shaped for contacting and desiccating tissue in a monopolar fashion. The cooling medium flowing internally through the uninsulated portion of the metallic conduit keeps the electrode in a cooled state during the electrosurgical procedure.

The bipolar loop cooling mechanism operates in a similar manner as that described above for the monopolar loop cooling mechanism, except that it is bipolar. Hence, an insulating tube is provided to separate the opposing electrode poles. That is, the insulating tube is integral with the conduit and, unlike the majority of the conduit which is conductive, the insulating tube is non-conductive. The bipolar isolated cooling mechanism does away with the insulating tube by providing two closed loop configurations, one for each electrode, each having a respective metallic conduit for delivering cooling medium to the electrodes situated in proximity to the distal end of the handset.

In one aspect of the present disclosure, an electrosurgical apparatus is adapted to connect to an electrosurgical energy source for performing surface tissue desiccation. The electrosurgical apparatus includes a handset having a shaft that extends therefrom that defines a longitudinal axis therethrough and at least one electrode provided in proximity to a distal end of the shaft. The electrosurgical apparatus further includes a cooling mechanism having one or more conduits coaxially disposed within the electrodes(s) for delivering a cooling fluid through the electrode(s) and returning the cooling fluid from the electrode(s) in a closed loop configuration to a fluid source. The electrosurgical apparatus is selected from the group consisting of monopolar and bipolar electrosurgical apparatuses.

The electrodes may include a first electrode and a second electrode. The conduit(s) is coaxially disposed within the first and second electrodes. The conduit(s) is separated from the first and second electrodes by an electrical insulator. The conduit(s) may be coated with an electrically insulative material. The conduit(s) couples to an insulator between the first and second electrodes. The conduits may be a first conduit for cooling the first electrode and a second conduit for cooling the second electrode. At least a portion of the conduit(s) may be metallic to provide good thermal conductivity to the electrode(s). The conduit(s) may be coaxially disposed within an electrical insulator. The electrical insulator, in turn, is coaxially disposed within the electrode(s). The conduit(s) is housed within a thermally insulative tubing except for a region of the conduit(s) in proximity to the electrode(s). The conduit(s) couples to an insulator between the first and second electrodes.

In another aspect of the present disclosure, there is provided an electrosurgical apparatus adapted to connect to an electrosurgical energy source for performing surface tissue desiccation. The electrosurgical apparatus includes a handset having a shaft that extends therefrom that defines a longitudinal axis therethrough and a first and a second electrode provided in proximity to a distal end of the shaft. The electrosurgical apparatus further includes a cooling mechanism having one or more conduits coaxially disposed within the first and second electrodes for delivering a cooling fluid to the first and second electrodes and returning the cooling fluid from the first and second electrodes in a closed loop configuration to a fluid source.

The conduit(s) couples to an insulator between the first and second electrodes. The conduit(s) is coaxially disposed within the first and second electrodes and separated by an electrical insulator. The conduit(s) includes a first conduit for cooling the first electrode and a second conduit for cooling the second electrode. At least a portion of the conduit(s) may be metallic to provide good thermal conductivity to the first and second electrodes. The conduit(s) is coaxially disposed within an electrical insulator, which, in turn, is coaxially disposed within the first and second electrodes. The conduit(s) is housed within a thermally insulative tubing except for a region of the conduit(s) in proximity to the first and second electrodes.

In an additional aspect of the present disclosure, there is provided a method for performing an electrosurgical procedure. The method includes providing an electrosurgical handset adapted to connect to an electrosurgical energy source. The handset includes a housing having a shaft that extends therefrom that defines a longitudinal axis therethrough and one or more electrodes at a distal end of the shaft. The method also includes the steps of: activating the energy source; causing the one or more electrodes to heat tissue; and internally cooling at least a portion of the one or more electrodes via a cooling mechanism, wherein the cooling mechanism supplies a cooling fluid to the one or more electrodes in a closed loop configuration. The electrosurgical apparatus may be selected from the group consisting of monopolar and bipolar electrosurgical apparatuses.

The one or more electrodes include a first electrode and a second electrode, and one or more conduits are coaxially disposed within the first and second electrodes for supplying the cooling fluid to the first and second electrodes. The one or more conduit(s) is separated from the first and second electrodes by an electrical insulator. The one or more conduits may be coated with an electrically insulative material. The one or more conduits couple to an insulator between the first and second electrodes. The conduits may include a first conduit for cooling the first electrode and a second conduit for cooling the second electrode. At least a portion of the conduits may be metallic to provide good thermal conductivity to the one or more electrodes. The one or more conduits are coaxially disposed within an electrical insulator, which, in turn, is coaxially disposed within the one or more electrode(s). The one or more conduit(s) may be housed within a thermally insulative tubing except for a region of the one or more conduit(s) in proximity to the electrodes.

As it is used herein, "electrosurgical procedure" generally refers to any electrosurgical procedure involving any form of energy, such as, for example, microwave energy and radiofrequency (RF) energy. As it is used herein, "desiccation" generally refers to electrosurgical desiccation which occurs when an electrode is in direct contact with tissue. Typically during electrosurgical desiccation no cutting action occurs, and the cells dry out and form a coagulum rather than vaporize and explode. As it is used herein, "surface tissue desiccation device" generally refers to an electrosurgical device capable of performing electrosurgical desiccation of surface tissue. As it is used herein, "fluid" generally refers to a liquid, a gas, a liquid containing a dissolved gas or dissolved gases, a mixture of gas and liquid, gas and suspended solids, liquid and suspended solids, or a mixture of gas, liquid and suspended solids.

The fluid can be conductive, such as saline, and the electrodes in at least one embodiment are isolated by an electrically insulating layer on the inside of the electrodes. Alternatively, the fluid may be non-conductive, such as organic fluids, for example, glycols or deionized water. The cooling reservoir may contain an ion exchanger for maintaining the deionized condition of the cooling fluid.

BRIEF DESCRIPTION OF THE DRAWING

Various aspects of the present disclosure are described hereinbelow with references to the drawings, wherein.

DETAILED DESCRIPTION

Detailed embodiments of the present disclosure are disclosed herein; however, it is to be understood that the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus, such as a surface tissue desiccation device, having an internal cooling mechanism that does not obscure the surgical site by dispensing cooling fluid onto the surgical site. An added advantage of the present disclosure, besides improving visibility to the surgical site, is that the internal cooling mechanism reduces the need for suction of the surgical site. Additionally, the closed-path configuration of the internal cooling mechanism in accordance with the present disclosure provides for less frequent refilling of the cooling medium. With this in mind, the present disclosure includes an electrosurgical handset for a surface tissue desiccation device that includes one or more electrodes in operative communication with a source of electrosurgical energy. Cooling fluid delivered by a cooling mechanism is used to keep the electrode(s) in a cooled state during an electrosurgical procedure.

The cooling mechanism according to the present disclosure includes a reservoir of cooling fluid, such as, a low conductive substance, e.g., a suitable sterile solution such as water, glycol, saline and the like, in fluid communication with a tubing or lumen for delivering the cooling fluid, such as saline, from the reservoir to the electrode(s). A pump may be used to pump the fluid from the reservoir to the electrode(s). In contrast to prior art cooling mechanisms for surface tissue desiccation devices, according to the present disclosure the tubing or lumen is self-contained, i.e., not open, which enables the cooling fluid to be delivered to the electrode(s) from the reservoir, and circulate back to the reservoir in a closed loop configuration, i.e., characterized herein as an internal cooling mechanism.

Figure 1:
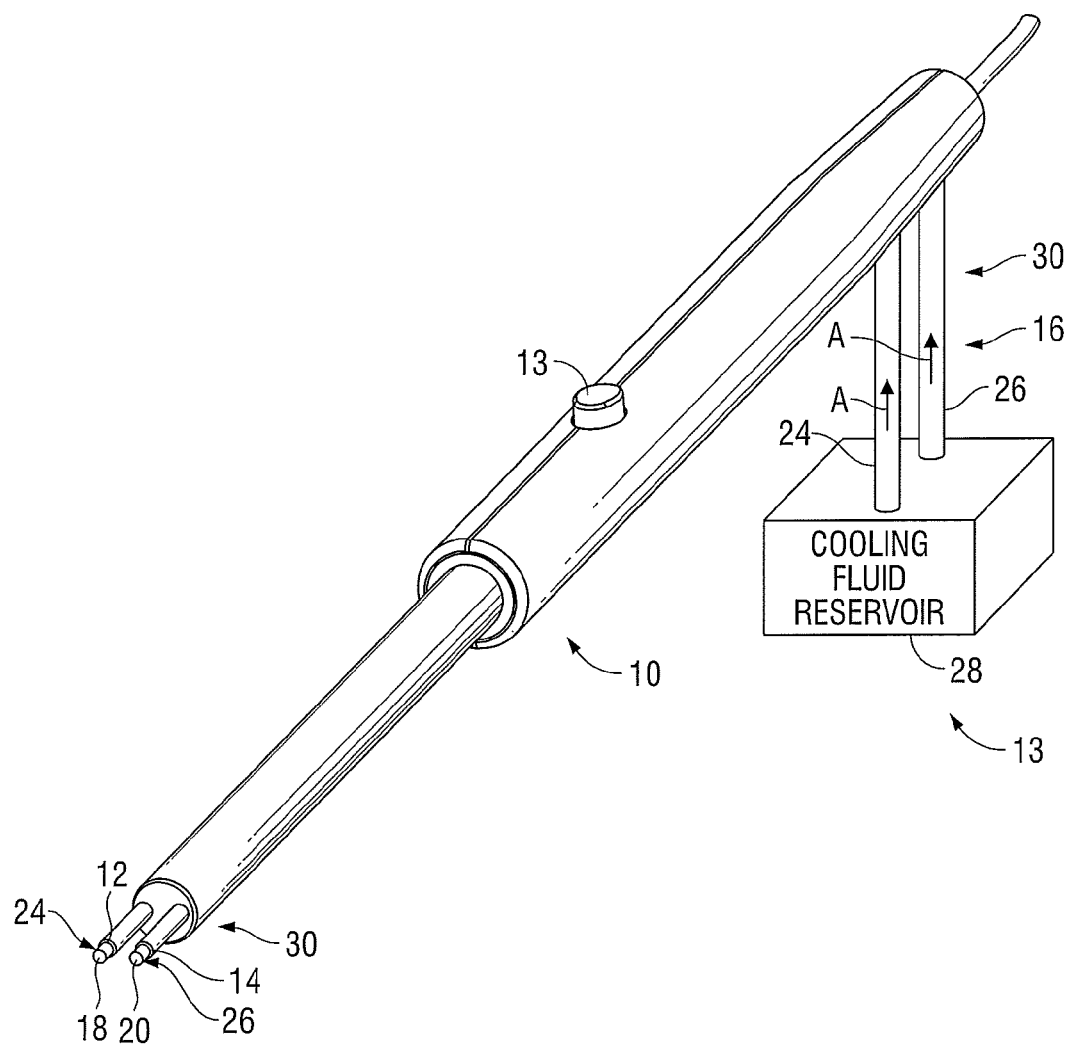
FIG. 1 is a perspective view of a prior art electrosurgical handset for a surface tissue desiccation device having a cooling mechanism which dispenses fluid from a distal end of the handset.
Figure 2A:
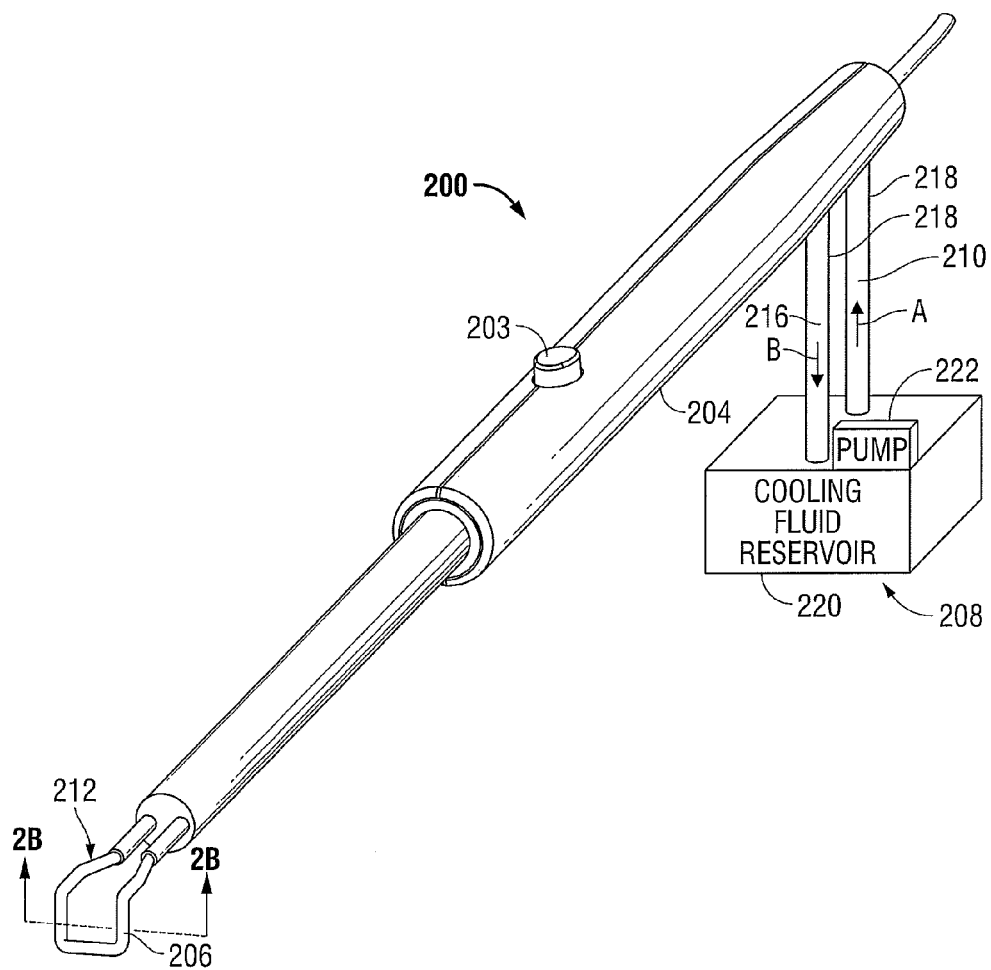
FIG. 2A is a perspective view of an electrosurgical handset for a surface tissue desiccation device having a monopolar loop cooling mechanism according to an aspect of the present disclosure.
Figure 2B:
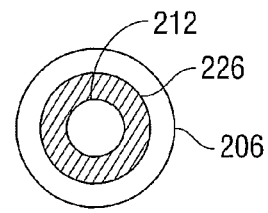
FIG. 2B is a cross-sectional view along line 2A-2A in FIG. 2A illustrating the inside of the tubing according to an aspect of the present disclosure.

With reference to FIG. 2, there is shown a perspective view of an electrosurgical apparatus according to an embodiment of the present disclosure and designated generally by reference numeral 200. The apparatus 200 includes a housing or handset 204 for performing surface tissue desiccation. The handset 204 includes an on/off switch 203, an electrode 206 and a monopolar loop cooling mechanism 208. The cooling mechanism 208 includes a tubing or lumen 210 having a conduit or fluid delivery tube 212 which may be made from a metal, such as steel, in fluid communication with a fluid reservoir or source 220 for delivering fluid to the electrode 206 as shown by arrow A in FIG. 2. The cooling mechanism 208 includes a pump 222 for pumping the cooling fluid through the fluid delivery tube 212.

The electrode 206 delivers electrosurgical energy to tissue during operation of the handset 200. The fluid delivery tube 212 traverses the length of the handset 204 and protrudes at a distal end thereof. The tube 212 is capable of internally delivering a cooling fluid to the electrode 206 for keeping the electrode 206 in a cooled state. The fluid delivery tube 212 is closed-ended thereby preventing the fluid from being dispensed onto the surgical site. The closed-ended tube 212 also enables the fluid to return via a return path 216 shown by arrow B in FIG. 2 to the fluid reservoir 220 which is then re-circulated back to the electrode 206.

The tubing 210 further includes a thermally insulative tubing 218 that houses the fluid delivery tube or conduit 212, except for the portion of the tube or conduit 212 delivering cooling fluid to the electrode 206, for preventing a user from contacting the heated metal. The tube or conduit 212 may be made from a material that is a very good electrical insulator to electrically insulate and isolate the tube 212 from the electrode 206. Alternatively, the material or electrical insulator 226 can be coaxially disposed within the electrode 206, i.e., provided between the tube or conduit 212 and electrode 206, as shown by FIG. 2A in order to isolate conductive types of cooling fluid from direct coupling to RF energy. Still, alternatively, an inner and/or outer surface of the tube 212 can be coated with an electrically insulative coating. The material, electrical insulator and/or coating should be a very poor thermal insulator such that the cooling fluid cools the electrode 206.

A cooling assembly (not shown) may be provided in operative communication with the reservoir 220 for cooling the cooling medium returning to the reservoir 220 from the heated electrode 206 during electrosurgery.

Figure 3A:
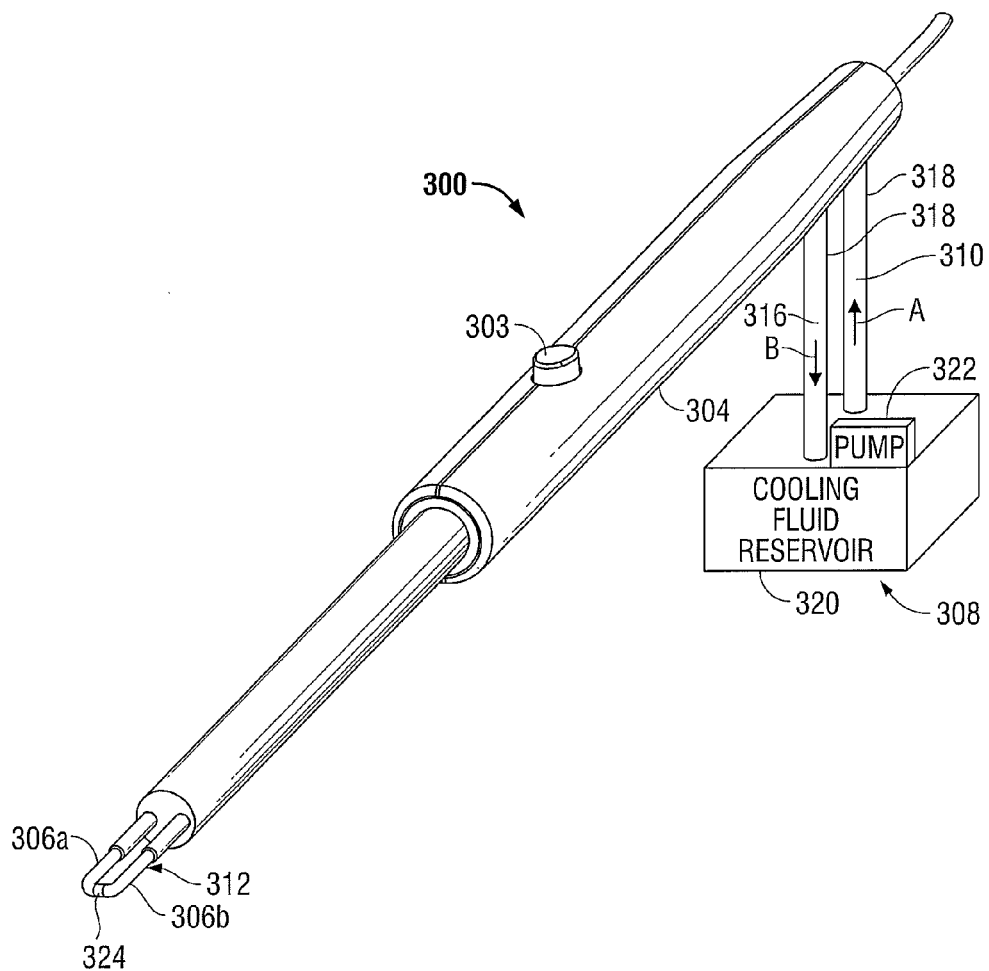
FIG. 3A is a perspective view of an electrosurgical handset for a surface tissue desiccation device having a bipolar loop cooling mechanism according to another aspect of the present disclosure.

With reference to FIG. 3A, there is shown a perspective view of an electrosurgical apparatus according to another embodiment of the present disclosure and designated generally by reference numeral 300. The apparatus 300 includes a housing or handset 304 for performing tissue desiccation. The handset 304 includes an on/off switch 303, two electrodes 306a, 306b and a bipolar loop cooling mechanism 308. The cooling mechanism 308 includes a tubing or lumen 310 having a conduit or fluid delivery tube 312 in fluid communication with a fluid reservoir or source 320 for delivering fluid to the electrodes 306a, 306b as shown by arrow A in FIG. 3A. The cooling mechanism 308 includes a pump 322 for pumping the cooling fluid through the fluid delivery tube 312.

The electrodes 306a, 306b deliver electrosurgical energy to tissue during operation of the handset 300. The fluid delivery tube 312 traverses the length of the handset 304 and protrudes at a distal end thereof for keeping the electrodes 306a, 306b in a cooled state via the cooling fluid pumped through the tube 312 by the pump 322. The fluid delivery tube 312 is closed-ended thereby preventing the fluid from being dispensed onto the surgical site. The closed-ended tube 312 also enables the fluid to return via a return path 316 shown by arrow B in FIG. 3A to the fluid reservoir and to be re-circulated back to the electrodes 306a, 306b.

Figure 3B:
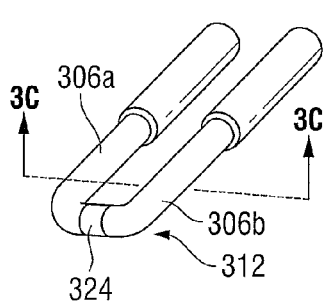
FIG. 3B is an enlarged distal view of the electrosurgical handset shown by FIG. 3A.
Figure 3C:
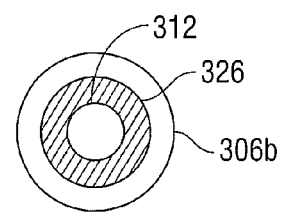
FIG. 3C is a cross-sectional view along line 3C-3C in FIG. 3B illustrating the inside of the tubing according to the present disclosure.

The tubing 310 further includes a thermally insulative tubing 318 that houses the fluid delivery tube 312, except for the portion of the tube or conduit 312 delivering cooling fluid to the electrodes 306a, 306b, for preventing a user from contacting the heated metal. The tube or conduit 312 may be made from a material that is a very good electrical insulator to electrically insulate and isolate the tube 312 from the electrodes 306a, 306b. The material or electrical insulator 326 can be coaxially disposed within the electrodes 306a, 306b and continuous with tube 310, i.e., provided between the tube or conduit 312 and electrodes 306a, 306b, as shown by FIGS. 3B and 3C for at least electrode 306b. Still, alternatively, an inner surface of the tube 312 can be coated with an electrically insulative coating. The material, electrical insulator and/or coating should be a very poor thermal insulator such that the cooling fluid cools the electrode 306a, 306b and continuous with tube 310.

A cooling assembly (not shown) may be provided in operative communication with the reservoir 320 for cooling the cooling medium returning to the reservoir 320 from the heated electrodes 306a, 306b during electrosurgery. The fluid delivery tube 312 may be made from metal, such as steel, except for a section/insulator 324 at a mid-point, as shown by FIGS. 3A and 3B which is made from an insulating material for providing electrical isolation between electrodes 306a, 306b at each end of the closed loop configuration. The fluid delivery tube 312 couples to the insulator 324 between electrodes 306a, 306b. This enables the handset 304 to be used in a bipolar configuration to treat tissue.

Figure 4A:
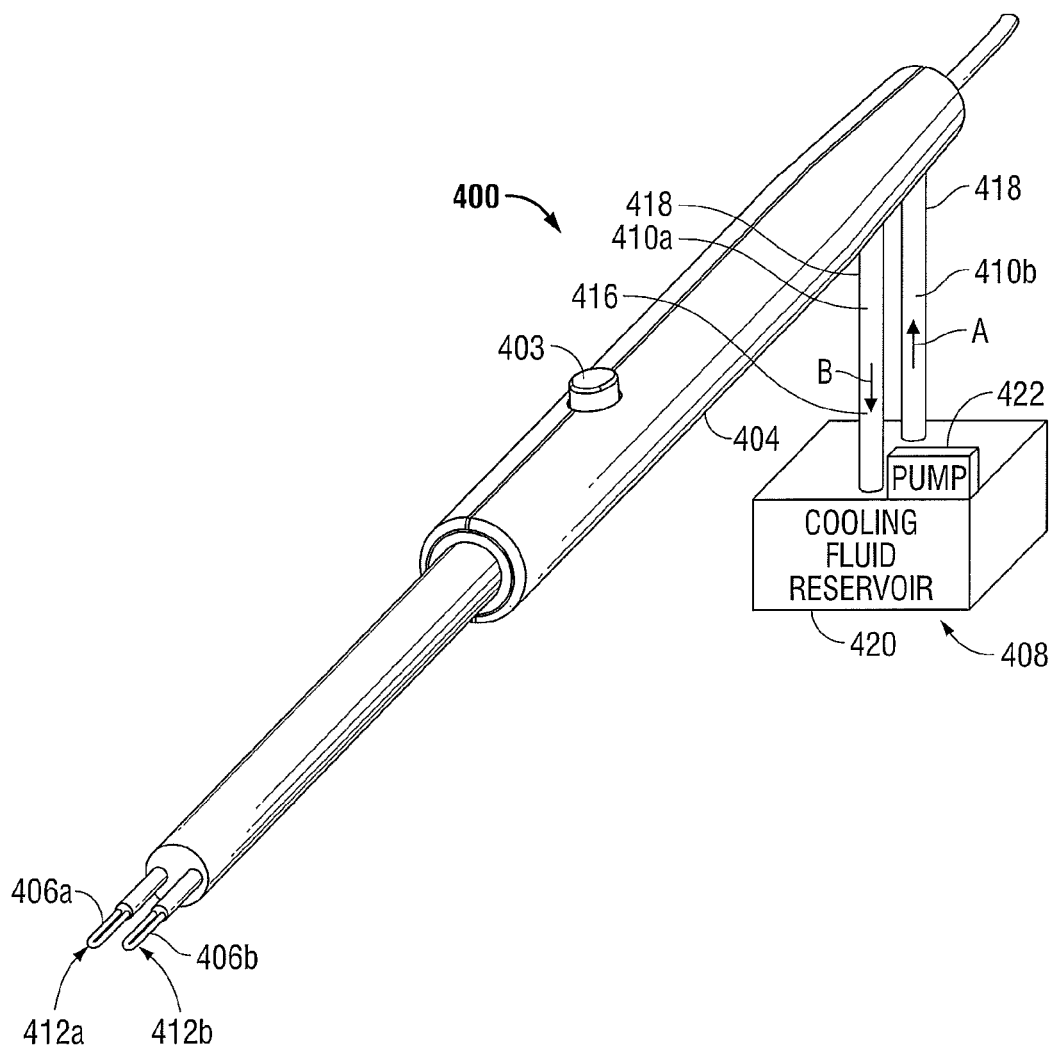
FIG. 4A is a perspective view of an electrosurgical handset for a surface tissue desiccation device having a bipolar isolated cooling mechanism according to still another aspect of the present disclosure.

With reference to FIG. 4A, there is shown a perspective view of an electrosurgical apparatus according to another embodiment of the present disclosure and designated generally by reference numeral 400. The apparatus 400 includes a housing or handset 404 for performing surface tissue desiccation. The handset 404 includes an on/off switch 403, two electrodes 406a, 406b and a bipolar isolated cooling mechanism 408. The cooling mechanism 408 includes two tubes or lumens 410a, 410b each having a respective fluid delivery tube 412a, 412b in fluid communication with a fluid reservoir or source 420 for delivering non-conductive fluid to the electrodes 406a, 406b. The tubes 410a, 410b may be made from a metal, such as steel. The cooling mechanism 408 further includes a pump 422 for pumping the non-conductive cooling fluid through the fluid delivery tubes 412a, 412b.

Figure 4B:
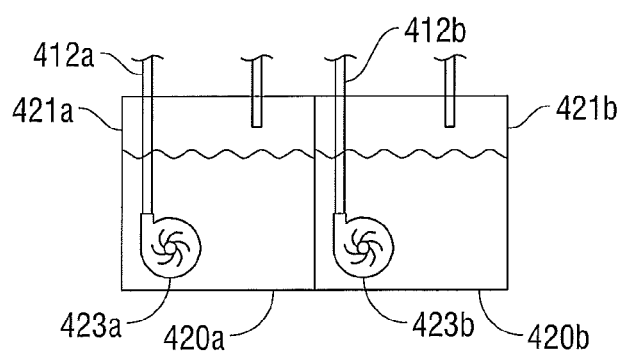
FIG. 4B is a phantom view showing an alternate embodiment for a cooling fluid reservoir.

Alternatively, a conductive water-based fluid may be used with a cooling reservoir 420a having two isolated fluid tanks 421a and 421b as shown in FIG. 4B. In this embodiment, tubes 412a and 412b have isolated cooling loops 423a and 423b running to the reservoir 420a. As can be appreciated, when using non-conductive fluids, such as 100% glycol, could be burdensome and the alternative cooling system of FIG. 4B may be of advantage.

The two electrodes 406a, 406b deliver electrosurgical energy to tissue during operation of the handset 400. The fluid delivery tubes 412a, 412b traverse the length of the handset 404 and protrude at a distal end thereof for keeping the electrodes 406a, 406b in a cooled state via the cooling fluid pumped through the tubes 412a, 412b by the pump 422. The tubes 412a, 412b are closed-ended thereby preventing the fluid from being dispensed onto the surgical site. The closed-ended tubes 412a, 412b also enable the fluid to return via a return path 416 shown by arrow B in FIG. 4A to the fluid reservoir 420 and then be re-circulated back to the electrodes 406a, 406b.

The tubes 410a, 410b further include a thermally insulative tubing 418 that houses the fluid delivery tubes 412a, 412b, except for the portion of the tubes 412a, 412b in proximity to the electrodes 406a, 406b, for preventing a user from contacting the heated metal.

A cooling assembly (not shown) may be provided in operative communication with the reservoir 420 for cooling the cooling medium returning to the reservoir 420 from the heated electrodes 406a, 406b during electrosurgery. The tubes or conduits 412a, 412b may be made from a material that is a very good electrical insulator to electrically insulate and isolate the tubes 412a, 412b from the electrodes 406a, 406b. Alternatively, the material or electrical insulator can be coaxially disposed within the electrodes 406a, 406b, i.e., provided between the tubes or conduits 412a, 412b and electrodes 406a, 406b, similarly to the embodiment shown by FIGS. 3B and 3C for at least electrode 306b. Still, alternatively, an inner surface of the tubes 412a, 412b can be coated with an electrically insulative coating. The material, electrical insulator and/or coating should be a very poor thermal insulator such that the cooling fluid cools the electrodes 406a, 406b. The fluid delivery tubes 412a, 412b may be also made from metal, such as steel.

The handsets 204, 304 and 404 may be operatively and selectively coupled to an electrosurgical generator (not shown) for performing electrosurgical procedures. The electrosurgical procedures may include cutting, cauterizing coagulating, desiccating, and fulgurating tissue; all of which may employ RF energy. Generator may be configured for monopolar and/or bipolar modes of operation. Generator may include or be in operative communication with a system that may include one or more processors in operative communication with one or more control modules that are executable on the processor. A control module (not shown) instructs one or more modules to transmit electrosurgical energy, which may be in the form of a wave or signal/pulse, via one or more cables.

The electrosurgical apparatus can be any suitable type of electrosurgical apparatus, including but not limited to electrosurgical apparatuses that can grasp and/or perform any of the above mentioned electrosurgical procedures.

At the same time that electrosurgical energy is supplied to electrode(s) 206, 306a, 306b, 406a, 406b, the fluid source is activated to supply coolant fluid through conduits 212, 312, 412a, 412b of respective electrode(s) 206, 306a, 306b, 406a, 406b for maintaining the outer peripheral surfaces of the respective electrode(s) 206, 306a, 306b, 406a, 406b in a relatively cooled state. Maintaining the outer peripheral surfaces of the electrode(s) 206, 306a, 306b, 406a, 406b in a cooled state helps prevent substantial thermal damage to surrounding tissue, thereby maintaining an electrically conductive path and preventing tissue from sticking to the electrode. The circulation of fluid through the conduits 212, 312, 412a, 412b may be configured to maintain respective outer peripheral surfaces of the electrode(s) 206, 306a, 306b, 406a, 406b at a temperature at or below 45° C. and, in some embodiments, below about 40° C. The electrode(s) 206, 306a, 306b, 406a, 406b may be coated with a conductive gel, saline solution, or other suitable substance (not explicitly shown) to help prevent the tissue from sticking to the electrode(s) 206, 306a, 306b, 406a, 406b.

Figure 5:
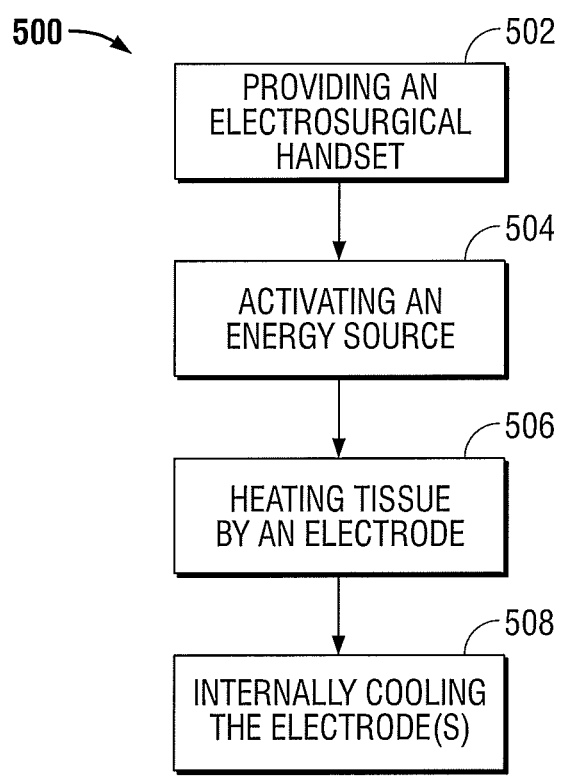
FIG. 5 is a flow chart diagram illustrating a method for performing an electrosurgical procedure according to the present disclosure.

FIG. 5 shows a method 500 for performing an electrosurgical procedure, especially surface tissue desiccation. The method includes the initial step of providing an electrosurgical handset adapted to connect to an electrosurgical energy source for performing an electrosurgical procedure (Step 502). The handset includes a housing having a shaft that extends therefrom that defines a longitudinal axis therethrough and at least one electrode at a distal end of the shaft adapted to be connected to the energy source.

The method includes the steps of: activating the energy source (Step 504); causing the at least one electrode to heat tissue (Step 506); and internally cooling at least a portion of the at least one electrode via a cooling mechanism (Step 508). The cooling mechanism supplies a cooling fluid to the at least one electrode in a closed loop configuration as described above with reference to FIGS. 2A-4.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical apparatus adapted to connect to an electrosurgical energy source for performing surface tissue desiccation, comprising:
   a handset having a shaft that extends therefrom that defines a longitudinal axis therethrough and at least one non-circular electrode extending substantially along a direction which is parallel to the longitudinal axis of the shaft and from a distal-most end of the shaft to a distance beyond the distal-most end of the shaft, such that a distal-most end of the apparatus is defined by a distal end of the at least one non-circular electrode; and a cooling mechanism having at least one conduit coaxially disposed within the at least one electrode for delivering a cooling fluid through the at least one electrode and returning the cooling fluid from the at least one electrode in a closed loop configuration to a fluid source.

2. An electrosurgical apparatus according to claim 1, wherein the electrosurgical apparatus is selected from the group consisting of monopolar and bipolar electrosurgical apparatuses.

3. An electrosurgical apparatus according to claim 1, wherein the at least one electrode includes a first electrode and a second electrode, and wherein the at least one conduit is coaxially disposed within the first and second electrodes.

4. An electrosurgical apparatus according to claim 3, wherein the at least one conduit is separated from the first and second electrodes by an electrical insulator.

5. An electrosurgical apparatus according to claim 1, wherein the at least one conduit is coated with an electrically insulative material.

6. An electrosurgical apparatus according to claim 3, wherein the at least one conduit couples to an insulator between the first and second electrodes.

7. An electrosurgical apparatus according to claim 1, wherein the at least one conduit includes a first conduit for cooling the first electrode and a second conduit for cooling the second electrode.

8. An electrosurgical apparatus according to claim 1, wherein at least a portion of the at least one conduit is metallic to provide good thermal conductivity to the at least one electrode.

9. An electrosurgical apparatus according to claim 1, wherein the at least one conduit is coaxially disposed within an electrical insulator.

10. An electrosurgical apparatus according to claim 9, wherein the electrical insulator is coaxially disposed within the at least one electrode.

11. An electrosurgical apparatus according to claim 1, wherein the at least one conduit is housed within a thermally insulative tubing except for a region of the at least one conduit in proximity to the at least one electrode.

12. An electrosurgical apparatus according to claim 1, wherein the cooling mechanism is electrically isolated from the user.

13. An electrosurgical apparatus according to claim 1, wherein the cooling fluid is a low conductive substance.

14. An electrosurgical apparatus adapted to connect to an electrosurgical energy source for performing surface tissue desiccation, comprising:

a handset having a shaft that extends therefrom that defines a longitudinal axis therethrough and a first and a second non-circular electrode extending substantially along a direction which is parallel to the longitudinal axis of the shaft and from a distal-most end of the shaft to a distance beyond the distal-most end of the shaft, such that a distal-most end of the apparatus is defined by a distal end of at least one of the non-circular first and second electrodes; and a cooling mechanism having at least one conduit coaxially disposed within the first and second electrodes for delivering a cooling fluid through the first and second electrodes and returning the cooling fluid from the first and second electrodes in a closed loop configuration to a fluid source.

15. An electrosurgical apparatus according to claim 14, wherein the at least one conduit couples to an insulator between the first and second electrodes.

16. An electrosurgical apparatus according to claim 14, wherein the at least one conduit is coaxially disposed within the first and second electrodes and separated by an electrical insulator.

17. An electrosurgical apparatus according to claim 14, wherein the at least one conduit includes a first conduit for cooling the first electrode and a second conduit for cooling the second electrode.

18. An electrosurgical apparatus according to claim 14, wherein at least a portion of the at least one conduit is metallic to provide good thermal conductivity to the first and second electrodes.

19. An electrosurgical apparatus according to claim 14, wherein the at least one conduit is coaxially disposed within an electrical insulator.

20. An electrosurgical apparatus according to claim 19, wherein the electrical insulator is coaxially disposed within the first and second electrodes.

21. An electrosurgical apparatus according to claim 19, wherein the at least one conduit is housed within a thermally insulative tubing except for a region of the at least one conduit in proximity to the first and second electrodes.

22. An electrosurgical apparatus according to claim 14, wherein the cooling mechanism is electrically isolated from the user.

23. An electrosurgical apparatus according to claim 14, wherein the cooling fluid is a low conductive substance.

* * * * *